(12) United States Patent
Nanjundaswamy et al.

(10) Patent No.: US 9,168,277 B2
(45) Date of Patent: Oct. 27, 2015

(54) NUTRACEUTICAL COMPOSITIONS PRODUCED FROM CO-PRODUCTS OF CORN OR MILO ETHANOL FERMENTATION AND METHODS OF MAKING AND USING THEREOF

(71) Applicants: Ananda K. Nanjundaswamy, Vicksburg, MS (US); Benedict C. Okeke, Montgomery, AL (US)

(72) Inventors: Ananda K. Nanjundaswamy, Vicksburg, MS (US); Benedict C. Okeke, Montgomery, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/202,266

(22) Filed: Mar. 10, 2014

(65) Prior Publication Data

US 2014/0271705 A1    Sep. 18, 2014

Related U.S. Application Data

(60) Provisional application No. 61/782,391, filed on Mar. 14, 2013.

(51) Int. Cl.
| | |
|---|---|
| A23K 1/06 | (2006.01) |
| A61K 36/06 | (2006.01) |
| A61K 31/366 | (2006.01) |
| A23K 1/16 | (2006.01) |
| A61K 36/062 | (2006.01) |

(52) U.S. Cl.
CPC . *A61K 36/06* (2013.01); *A23K 1/06* (2013.01); *A23K 1/164* (2013.01); *A61K 31/366* (2013.01); *A61K 36/062* (2013.01); *A61K 2236/00* (2013.01)

(58) Field of Classification Search
None
See application file for complete search history.

(56) References Cited

U.S. PATENT DOCUMENTS

| | | | |
|---|---|---|---|
| 4,418,080 | A | 11/1983 | Yueh et al. |
| 4,418,081 | A | 11/1983 | Rashbaun |
| 4,927,760 | A | 5/1990 | Martin |
| 6,046,022 | A | 4/2000 | Zhang et al. |
| 6,316,041 | B1 | 11/2001 | Stock et al. |
| 6,613,365 | B1 | 9/2003 | Yamamoto |
| 7,157,107 | B2 | 1/2007 | Pan et al. |
| 2002/0061547 | A1 | 5/2002 | Chen et al. |
| 2003/0194394 | A1 | 10/2003 | Hong et al. |
| 2007/0244719 | A1 | 10/2007 | David |
| 2009/0181150 | A1 | 7/2009 | Kim et al. |

FOREIGN PATENT DOCUMENTS

| | | |
|---|---|---|
| WO | 2004030632 | 4/2004 |
| WO | 2012078256 | 6/2012 |

OTHER PUBLICATIONS

Nanjundaswammy et al, (2010a) Production and optimization of carotenoid-enriched distillers dried grain with solubles by *Phaffia rhodozyma* and *Sporobolomyces roseus* fermentation of whole still-age. Journal of Industrial Microbiology and Biotechnology 37:1183-1192 (DOI: 10.1007/s10295-010-0765-y).

Ananda N, Vadlani PV (2010b) Fiber reduction and lipid enrichment in carotenoid-enriched distillers dried grain with solubles (DDGS) by secondary fermentation of red yeasts. Journal of Agricultural and Food Chemistry. DOI:10.1021/jf103129t.

Chen et al, 2008. Red mold rice prevents the development of obesity, dyslipidemia and hyperinsulinemia induced by high-fat diet. Intl J Obesity. 32: 1694-1704.

Chen et al, 2011. Isolation and characterization of a strain of *Klebsiella pnuemoniae* with citrinin-degrading activity. World J Microbiol Biotechnol 27: 487-493.

De Godoy et al, 2009. Select corn coproducts from ethanol industry and their potential as ingredients in pet foods. J Anim SCi 87: 189-199.

Jang et al, 2007. Effects of solid-state fermented rice on lipid metabolism and antioxidant status in high-cholesterol-fed rats. J Med Food 10(4): 608-614.

Jannoey et al, 2010. Comparison of gama aminobutyric acid production in Thai rice grains. World J. Microbiol Biotechnol. 26: 257-263.

Kuo et al, 2008. Downregulation of hepatic lipoprotein assembly in rats by fermented products of *Monascus pilosus*. Nutrition 24: 477-483.

Lee YL, Yang JH, Mau JL. 2009. Antioxidant properties of ethanolic and methanolic extracts from *Monascus*-fermented soybeans. J Food Chem 33: 707-727.

Li et al, *Monascus purpureus*-fermented rice (red yeast rice): a natural product that lowers blood cholesterol in animal models of hypercholesterolemia, Nut Res 18(1):71-81, 1998.

Lu et al, 2009. Optimization of fermentative parameters for GABA enrichment by *Lactobacillus lactis*. Czech J Food Sci 27(6): 433-442.

(Continued)

*Primary Examiner* — Brian J Gangle
(74) *Attorney, Agent, or Firm* — Gardner Groff Greenwald & Villanueva, PC (57) ABSTRACT

Described herein is a process for producing nutraceutical compositions that includes fermenting a species of *Monascus* in the presence of one or more co-products produced during corn ethanol fermentation, milo ethanol fermentation, or a combination thereof. During fermentation, the *Monascus* species produces valuable nutraceuticals that have numerous health benefits. In one aspect, the nutraceutical composition containing the microbial cells and nutraceuticals is then processed directly into animal feed in order to improve animal health. The processes and compositions described herein represent significant savings of time and materials and optionally make use of co-products of biofuel production. In other aspects, one or more nutraceuticals can be extracted from the nutraceutical composition and used to improve human health in pharmaceutical applications.

16 Claims, 2 Drawing Sheets

(56) References Cited

OTHER PUBLICATIONS

Manzoni M, Rollini M. 2002. Biosynthesis and biotechnological production of statins by filamentous fungi and application of these cholesterol-lowering drugs. Appl Microbiol Biotechnol 58:555-564.

Monhan Kumari et al, 2009. Safety evaluation of *Monascus purpureus* red mould rice in albino rats. Food Chem Tox 47:1739-1746.

Mukherjee et al, 2011. Purification and characterization of a new red pigment from *Monascus purpureus* in submerged fermentation. Process Biochemistry 46: 188-192.

Panda et al, 2009. Statistical analysis and validation of process parameters influencing lovastatin production by *Monascus purpureus* MTCC 369 under soli-state fermentation. Biotechnol Bioprocess Engg 14:123-127.

Rajasekaran et al, 2011. Hypolipidemic and antioxidant activity of aqueous extract of *Monascus purpureus* fermented Indian rice in high cholesterol diet fed rats. Turk J Med Sci 41(1): 25-32.

Sennevasan et al, 2008. Microbial production and biomedical applications of lovastatin. Indian J Pharma Sci. 70(6) 701-709.

Shi Y, Pan T. 2010. Anti-diabetic effects of *Monascus purpureus* NTU 568 fermented products on Streptozotocin-induced diabetic rats. J agric Food Chem.: 58:7634-7640.

Shin et al, 1998. Morphological change and enhanced pigment production of *Monascus* when cocultured with *Saccharomyces cerevisiae* or *Aspergillus oryzae*. Biotechnol Bioeng 59:576-581.

Subhagar et al, 2009. Response surface optimization of mixed substrate soli-state fermentation for the production of lovastatin by *Monascus purpureus*. Eng Life Sci 9(4): 303-310.

Tsukahara, 2009. Red yeast rice fermentation by selected *Monascus* sp. with deep-red color, lovastatin production but no citrinin and effect of temperature shift cultivation on lovastatin production. Appl Biochem Biotechnol 158:476-482.

US Grains Council (2007) DDGS User Handbook. Washington, USA.

Wang et al, 2006. Effect of red mold rice supplements on serum meat cholesterol levels of broilers chicken. Appl Microbiol Biotechnol 71: 812-818.

Wei et al, 2003. Hypolipidemic and anti-antherogenic effects of long-term cholestin (*Monascus purpureus*-fermented rice, red yeast rice) in cholesterol-fed rabbits. J Nut Biochem. 14: 314-318.

Wu et al, 2011. Synchronous high performance liquid chromatography with a photodiode array detector and mass spectrometry for the determination of citrinin, monascin, ankaflavin and the lactone and acid forms of monacolin K in red mold rice. J AOAC Intl 94(1):179-190.

Xu et al, 2006. Review on the qualitative and quantitative analysis of the mycotoxin citrinin. Food Control 17:271-285.

Jiang D, Ji H, Hou J. 2011. Studies on screening higher gama-aminobutyric acid-producing *Monascus* and optimization of fermentative parameters. Eur. Food. Res. Technol. 232:541-547.

Kim et al, 2010. L-Trp and L-Leu-Et derivatives of the *Monascus* pigment exert high anti-obesity effects on mice. Biosci Biotechnol Biochem. 74: 304-308.

Kongruang, 2011. Growth kinetics of biopigment production by Thai isolated *Monascus purpureus* in a stirred tank bioreactor. J Ind Microbiol Biotechnol 38:93-99.

Negishi S et al. 1986. Productivity of monacolin K (mevinolin) in the genus *Monascus*. J Ferment Eng 64:509-551. Abstract Only.

NUTRACEUTICAL COMPOSITIONS PRODUCED FROM CO-PRODUCTS OF CORN OR MILO ETHANOL FERMENTATION AND METHODS OF MAKING AND USING THEREOF

CROSS REFERENCE TO RELATED APPLICATION

This application claims the benefit of U.S. Provisional Application Ser. No. 61/782,391 filed on Mar. 14, 2013. This previous application is hereby incorporated by reference in its entirety for all of its teachings.

BACKGROUND

Red yeast rice, also known as red mold rice, is a fermented product of the fungus *Monascus purpureus* (also known as red yeast or red mold), using rice as a feedstock. Red yeast rice has been used in ethnomedicine for thousands of years in China and elsewhere in Asia. Secondary metabolites of *Monascus* fermentation include monacolin K (also known as lovastatin), gamma-aminobutyric acid (GABA), the antioxidant dimerumic acid and a variety of pigments.

Monacolin K is produced by at least 17 of the 124 known *Monascus* strains; among these are *M. ruber, M. purpureus, M. pilosus, M. vitreus, M. pubigerus,* and *M. anka*. This compound inhibits cholesterol biosynthesis and is also known to regulate inflammatory and immunological responses, coagulatory processes, bone turnover, neovascularization, vascular tone, and arterial pressure.

GABA, which acts as an inhibitory neurotransmitter in mammals, is antihypertensive, diuretic, and tranquilizing. It further regulates blood pressure, heart rate, sensations of pain and anxiety, and lipid levels in serum and can prevent diabetes and inhibit cancer cell proliferation. GABA supplementation has been demonstrated to calm and de-stress animals such as race horses when they are subjected to, for example, crowding situations.

Pigments produced by *Monascus* include rubropunctamine, monoscorubramine, monascin, ankaflavin, rubropunctain, and monascorubin; new *Monascus* pigments are still being discovered. These pigments impart color and have been reported to possess immunosuppressive, antioxidant, antibiotic, antimalarial, antitubercular, and antitumor properties.

The health benefits of many of the above-listed secondary metabolites are well-studied. Treatment with red yeast rice has been shown to suppress atherosclerosis in both mammalian and avian models. Poultry that are given feed supplemented with red yeast rice produce meat with lower cholesterol and higher levels of unsaturated fatty acids, and produce eggs with lower cholesterol levels.

While the mycotoxin citrinin produced by *Monascus* is reported to be nephrotoxic, the practice of feeding *Monascus*-fermented products to animals is generally recognized as safe. Additionally, fermentation can be optimized to reduce or eliminate the production of citrinin and/or other toxins.

Solid state fermentation has been employed to produce monacolin K from *Monascus* cultures; yields vary based on type of substrate, type of fermentation, and growth conditions. Mixed fermentation with other microbial species has been demonstrated to lead to increased pigment production.

Dried distillers grain with solubles (DDGS) is produced from whole stillage, a co-product of corn ethanol fermentation. Production of DDGS is expected to rise with increasing demand for biofuels. DDGS has found use primarily as animal feed, particularly for cattle, swine, poultry, and in aquaculture. In the US, DDGS production was 39.27 million short tons for 2012-2013; this number is projected to rise to 41.23 to 43.78 million short tons for 2013-2014.

While red yeast rice powder or microbial cultures have been used to supplement animal feeds in the past, these products have the disadvantage of being difficult and expensive to produce. First, a *Monascus* species must be cultivated in order to produce desired secondary metabolites. Then, the yeast culture must be processed in order to extract and purify the metabolites. Extraction and purification must be completed for each metabolite to be added to the feed. Finally, the metabolites must be added to an existing animal feed product. These extra processing steps add time and expense and, ultimately, add cost to the final feed products that are produced. Moreover, rice is a staple human food in many countries and its use for *Monoascus* fermentation will negatively impact human food supply. Thus, it would be desirable to eliminate some of the steps currently used to produce nutraceutically-enhanced animal feeds in order to save costs. Ideally, these feeds could be used with a variety of livestock and non-livestock animals for the purpose of enhancing the health of the animals and/or increasing the nutritional and health qualities of products produced by the animals (i.e., meat, eggs, dairy, and/or poultry). Further, it would also be desirable to provide a new source of and method for extracting nutraceuticals to be used as food supplements, additives, and/or medicines for humans and animals. Finally, if a new market could be developed for existing biofuel co-products and wastes, the long-term sustainability of biofuels could be ensured. The present invention addresses these needs.

SUMMARY

Described herein is a process for producing nutraceutical compositions that includes fermenting a species of *Monascus* in the presence of one or more co-products produced during corn ethanol fermentation, milo ethanol fermentation, or a combination thereof. During fermentation, the *Monascus* species produces valuable nutraceuticals that have numerous health benefits. In one aspect, the nutraceutical composition containing the microbial cells and nutraceuticals is then processed directly into animal feed in order to improve animal health. The processes and compositions described herein represent significant savings of time and materials and optionally make use of co-products of biofuel production. In other aspects, one or more nutraceuticals can be extracted from the nutraceutical composition and used to improve human health in pharmaceutical applications.

The advantages of the materials, methods, and devices described herein will be set forth—in part in the description which follows—or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The compositions, methods, and articles described herein can be understood more readily by reference to the following detailed description. It is also to be understood that the terminology used herein is for the purpose of describing particular aspects only and is not intended to be limiting.

It must be noted that, as used in the specification and the appended claims, the singular forms "a," "an," and "the" include plural referents unless the context clearly dictates otherwise. Thus, for example, reference to "a fatty acid" includes mixtures of two or more fatty acids.

"Optional" or "optionally" means that the subsequently described event or circumstance can or cannot occur and that the description includes instances where the event or circumstance occurs and instances where it does not. For example, the phrase "optionally includes a second microbial species" means that the second microbial species can or cannot be included.

As used herein, the term "about" is used to provide flexibility to a numerical range endpoint by providing that a given value may be "a little above" or "a little below" the endpoint without affecting the desired result.

"Nutraceutical" refers to a substance that provides health benefits or possesses medicinal value and that can also have nutritional value. The term "nutraceutical" also refers to secondary metabolites produced during the processes described herein.

"Fermenting" and "fermentation" refer to the growth of microorganisms in or on a culture medium, a growth medium, a feedstock, or a combination thereof. During fermentation, microorganisms consume nutrients from the culture medium, growth medium, or feedstock and produce useful metabolites, which may be extracted and purified. Several different methods of fermentation are commonly employed. In "batch fermentation," all components necessary for the fermentation (microorganisms, feedstock, water, nutrients, etc.) are introduced into the bioreactor at the beginning of a run and remain there until the end. In "fed-batch fermentation," meanwhile, one or more nutrients may be supplied to the bioreactor during the run. In "continuous fermentation," fresh nutrient solution is continually added to a bioreactor as equivalent amounts of converted medium are removed. In "solid state fermentation," a solid, porous substrate is deposited and seeded with microorganisms; this substrate is capable of absorbing water and air circulation around the substrate and growing microbial culture is carefully managed. In "semi-solid fermentation," a solid mash or substrate is suspended in a liquid medium; motile microorganisms are able to move through the medium. Finally, in "submerged fermentation," the microorganisms being cultured are submerged in a liquid medium. These fermentation methods are not mutually exclusive and a given fermentation may, itself, be a hybrid of two or more fermentation types.

"Co-product" as used herein, is one or more by-products produced during corn ethanol fermentation, milo ethanol fermentation, or a combination thereof. Co-products of these fermentation processes include whole stillage, thin stillage, wet cake, distiller grains, dried distiller grains, and dried distillers grains with solubles (DDGS).

"Whole stillage" is the remaining wet mash produced after corn ethanol fermentation and milo ethanol fermentation. The whole stillage can be further processed as needed.

"Dried distillers grains with solubles" or DDGS is a byproduct or co-product of the distillation process, such as from breweries or biofuel fermentation plants. After alcoholic fermentation is completed, unfermented grain residues may remain. These typically contain a high moisture level but can be concentrated or dried to provide a lower moisture content (i.e., 10-12%), forming DDGS. DDGS has a long shelf life and can be used as feed for livestock or other animals.

A "pigment" is a highly colored molecule. Pigments can be complex organic molecules such as those produced by plants and microorganisms, and may be valued for their color and/or nutritional and medicinal properties. Pigments work by changing the color of light reflected from an object due to their absorption of certain wavelengths of light.

As used herein, "acid detergent fiber" represents the least digestible fiber portion of forage or other roughage. This highly indigestible part of forage and includes lignin, cellulose, silica and insoluble forms of nitrogen but not hemicellulose.

As used herein, "neutral detergent fiber" represents the residue or insoluble fraction left after boiling a feed sample in neutral detergent solution.

The compounds and compositions described herein can be used "as-is" or can be further extracted and/or purified to concentrate desired metabolites. "Extraction" as used herein is a process by which a substance (i.e., a nutraceutical) is extracted from a matrix (i.e., a feedstock). Common extraction techniques include, but are not limited to, liquid-liquid extraction and solid phase extraction. "Purification" as used herein is a process by which a compound or metabolite in an impure (i.e., mixed with other compounds or contaminating substances) state is physically separated from impurities. Purification techniques include, but are not limited to, recrystallization, sublimation, distillation, extraction, chromatography, filtration, centrifugation, and combinations thereof.

Following microbial fermentation, the nutraceutical compositions disclosed herein may, in some aspects, contain moisture. "Drying" can optionally be carried out on these products and compositions to reduce the moisture level. Examples of drying processes that can be used include, but are not limited to, freeze drying, oven drying, and sun drying.

As used herein, "animal feed" means a product or composition of primarily biological origin that can be consumed by an animal and that provides nutrition for that animal. An animal feed may be a "compound feed" that is blended from multiple raw materials and is generally formulated to meet the specific needs of a target animal. An animal feed can take any form commonly used in industry, including pellets, cakes, meal, crumbles, granules, and so forth. An animal feed can be supplemented with vitamins, minerals, preservatives, antibiotics, amino acids, pigments, and other additives; these supplements may be supplied as part of a commercial feed or as additives used by farmers, ranchers, and herders on grains purchased or grown separately.

As used herein, "animal" includes mammals, reptiles, and amphibians. Examples of animals include pets, livestock, ruminants, and non-ruminants.

A "pet" is any animal kept for companionship or protection purposes and may include dogs, cats, rabbits, reptiles, tropical fish, frogs, rodents (including rats, mice, hamsters, gerbils, and guinea pigs), potbellied pigs, and birds (including finches, canaries, and parrots). In some cases, pets may also act as working animals or sporting animals.

"Livestock" refers to domesticated animals that are raised to produce food such as meat, poultry, eggs, or dairy; to produce fiber and wearable material such as wool, fur, hair, or leather; or to perform work such as providing transportation for people or goods. Examples of livestock include, but are not limited to, cattle, horses, sheep, pigs, and chickens.

A "ruminant" is an animal that possesses a specialized stomach called a "rumen," wherein plant-based food is fermented through bacterial action prior to further digestion. Food that has been ingested and fermented may be regurgitated and chewed again prior to the completion of digestion. The stomachs of ruminant mammals have four chambers. Ruminant animals include, but are not limited to, cows, goats, and sheep. "Non-ruminant" or "monogastric" animals, meanwhile, have stomachs with only a single compartment. Non-ruminant animals may be herbivores, omnivores, or carnivores.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group, without indications to the contrary.

As used herein the term "enhance" means an improvement of one or more properties relative to a control. For example, the methods described herein increase the production of one or more nutraceuticals when a co-product is fermented with a species of *Monascus* when compared to the same co-product that is not fermented with a species of *Monascus*.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range was explicitly recited. As an illustration, a numerical range of "about 1 to about 5" should be interpreted to include not only the explicitly recited values of about 1 to about 5, but also to include individual values and sub-ranges within the indicated range. Thus, included in this numerical range are individual values such as 2, 3, and 4, the sub-ranges such as from 1-3, from 2-4, from 3-5, etc., as well as 1, 2, 3, 4, and 5, individually. The same principle applies to ranges reciting only one numerical value as a minimum or a maximum. Furthermore, such an interpretation should apply regardless of the breadth of the range or the characteristics being described.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a *Monascus* species is disclosed and discussed and a number of different feedstocks are discussed, each and every combination of *Monascus* species and feedstock that is possible to be specifically contemplated unless specifically indicated to the contrary. For example, if a class of molecules A, B, and C are disclosed, as well as a class of molecules D, E, and F, and example of a combination A+D is disclosed, then even if each is not individually recited, each is individually and collectively contemplated. Thus, in this example, each of the combinations A+E, A+F, B+D, B+E, B+F, C+D, C+E, and C+F, are specifically contemplated and should be considered disclosed from disclosure of A, B, and C; D, E, and F; and the example combination of A+D. Likewise, any subset or combination of these is also specifically contemplated and disclosed. Thus, for example, the subgroup of A+E, B+F, and C+E is specifically contemplated and should be considered from disclosure of A, B, and C; D, E, and F; and the example combination of A+D. This concept applies to all aspects of this disclosure including, but not limited to, steps in methods of making and using the disclosed compositions. Thus, if there are a variety of additional steps that can be performed with any specific embodiment or combination of embodiments of the disclosed methods, each such combination is specifically contemplated and should be considered disclosed.

Preparation and Characterization of Nutraceutical Compositions

In one aspect, nutraceutical compositions are produced as a result of the fermentation of a species of *Monascus* in the presence of one or more co-products produced during corn ethanol fermentation, milo ethanol fermentation, or a combination thereof. In one aspect, the nutraceutical may already present at a low level in the co-product but the microbial fermentation increases production of the nutraceutical. In other aspects, the nutraceutical of interest is not initially present in the feedstock and the microbial fermentation serves to introduce the nutraceutical into the nutraceutical composition.

In one aspect, the species of *Monascus* is *Monascus ruber*, *Monascus purpureus*, *Monascus pilosus*, *Monascus vitreus*, *Monascus pubigerus*, *Monascus anka*, or a combination thereof. In another aspect, the species of *Monascus* is pigmented *Monascus purpureus*, a non-pigmented *Monascus purpureus*, or a combination thereof.

The co-product can be fermented with the species of *Monascus* using techniques known in the art. In one aspect, the co-product is corn whole stillage or milo whole stillage. The fermentation process can be optimized to produce a higher amount of a desired fermentation product or products. In a further aspect, optimization can be achieved by using different feedstocks as described above, or different additives such as additional carbon sources, nitrogen sources, enzymes, trace elements and minerals, vitamins, vitamin precursors, and combinations thereof.

In another aspect, one or more additional microbial strains can be used in combination with the species of *Monascus*. In this aspect, the additional microbial strain can be an alga, a bacterium, or a fungus. In one aspect, the bacterium is a *Lactobacillus* species or a *Streptomyces* species. In another aspect, the fungus is *Saccharomyces cerevisiae* or *Aspergillus oryzae*. Not wishing to be bound by theory, the additional microbial strain(s) performs a beneficial function such as producing one or more desired additional nutraceuticals, breaking down a component of the co-product for easier accessibility by the *Monascus* species.

In another aspect, fermentation conditions can be altered to achieve optimal production of a desired product. For example, the fermentation type can be changed. Fermentation types include, but are not limited to, batch fermentation, fed-batch fermentation, continuous fermentation, semi-solid fermentation, solid-state fermentation, submerged fermentation, and combinations thereof. In a further aspect, fermentation conditions can be modified to optimize production of a desired product. In this aspect, fermentation conditions to be modified can include, but are not limited to, temperature, pH, aeration, stirring speed, light conditions, fermentation time, and combinations thereof.

After the co-product has been fermented with a species of *Monascus*, the nutraceutical composition can be further processed as needed. In one aspect, the nutraceutical can be subjected to a drying process prior to use. In this aspect, drying techniques such as, for example, oven drying, freeze drying, or sun drying can be used. In another aspect, prior to or following drying, or in the absence of drying, the nutraceutical composition can be extruded and/or further processed to form pellets, granules, powder, or meal when incorporated into an animal feed.

The production of desired nutraceuticals is enhanced using the methods described herein. In one aspect, the desired nutraceuticals include, but are not limited to, crude protein, free amino acids, bound amino acids, peptides, pigments, vitamins, neurotransmitters, HMG-CoA reductase inhibitors, free fatty acids, triglycerides, other lipids, complex carbohydrates, simple carbohydrates, and any combination thereof.

In one aspect, production of pigments can be enhanced using the methods described herein. In this aspect, the pigments can be, but are not limited to, astaxanthin, beta-carotene, rubropunctamine, monoscorubramine, monascin, ankaflavin, rubropunctain, monascorubin, or a combination thereof. In a further aspect, the pigments provide color that may entice a human or animal to eat. In still another aspect, the pigments may remain in animal tissue and enhance the color of that tissue, which can potentially provide additional color to meat products produced from the animals that consumed the pigments. In another aspect, the pigments, themselves, have nutritional value as vitamins, micronutrients, or phytochemicals, or may possess organoleptic properties.

In one aspect, production of neurotransmitters can be enhanced using the methods described herein. In another aspect, the neurotransmitters are biogenic amines and/or amino acids. In a further aspect, the neurotransmitter is gamma-aminobutyric acid (GABA) or a related molecule. In these aspects, consumption by a human or animal of a food or animal feed product containing a feedstock that has been microbially-fermented is beneficial to the consumer due to the presence of the neurotransmitter(s). In one aspect, the neurotransmitter acts as an antihypertensive, a diuretic, or a tranquilizer. In another aspect, the neurotransmitter regulates blood pressure, heart rate, sensations of pain and anxiety, or lipid levels in serum. In still another aspect, the neurotransmitter reduces the likelihood of developing diabetes and/or inhibits cancer cell proliferation.

In one aspect, production of HMG-CoA reductase inhibitors (i.e., statins) can be enhanced using the methods described herein. In one aspect, the HMG-CoA reductase inhibitor is monacolin K (i.e., lovastatin) or the monacolin K precursor mevalonic acid. In one aspect, consumption of a product with increased levels of a statin or statins improves human or animal health, for example, by decreasing cholesterol levels. In another aspect, consumption of a product with increased levels of a statin or statins results in an animal product (such as dairy, meat, poultry, or eggs) with a lower cholesterol level. In this aspect, consumption of the animal product by a human or other animal can also lead to lower cholesterol levels in the human or other animal.

In one aspect, production of one or more carbohydrates can be enhanced using the methods described herein. In a further aspect, the carbohydrates can be simple or complex carbohydrates. In one aspect, the simple carbohydrates include glucose, mannose, glucosamine, and combinations thereof. In another aspect, the complex carbohydrates include acid detergent fiber and/or neutral detergent fiber (i.e., lignin, cellulose, hemicellulose, and combinations thereof). In a further aspect, the complex carbohydrates include xylan, xanthan gum, starch, pectin, guar gum, and combinations thereof. In some aspects, both simple and complex carbohydrate levels increase as a result of microbial fermentation. In other aspects, both simple and complex carbohydrate levels decrease as a result of microbial fermentation. In still other aspects, complex carbohydrate levels increase as a result of microbial fermentation, while simple carbohydrate levels decrease. In other aspects, the levels of individual sugars and amino sugars do not follow the same trend (i.e., increasing or decreasing) as other individual sugars and amino sugars.

In one aspect, when corn whole stillage is fermented with *Monascus purpureus*, the nutraceutical composition has from 700% to 1,000% by weight more glucosamine compared to the same co-product not fermented with *Monascus purpureus*. In another aspect, when corn whole stillage is fermented with *Monascus purpureus*, the nutraceutical composition has from 150% to 400% by weight more mannose compared to the same co-product not fermented with *Monascus purpureus*. In a further aspect, when corn whole stillage is fermented with *Monascus purpureus*, the nutraceutical composition has from 25% to 75% by weight more glucose compared to the same co-product not fermented with *Monascus purpureus*.

In other aspects, the methods described herein can enhance the production of fibrous materials. In one aspect, when corn whole stillage is fermented with *Monascus purpureus*, the nutraceutical composition has from 75% to 250% by weight more acid detergent fiber compared to the same co-product not fermented with *Monascus purpureus*. In another aspect, when corn whole stillage is fermented with *Monascus purpureus*, the nutraceutical composition has from 25% to 75% by weight more neutral detergent fiber compared to the same co-product not fermented with *Monascus purpureus*.

In some aspects, production of one or more amino acids can be enhanced using the methods described herein. In a further aspect, both crude protein levels and amounts of individual amino acids can be enhanced. In an alternative aspect, crude protein levels decrease but levels of free amino acids increase. In another aspect, the amino acid with increased production may be selected from proteinogenic or non-proteinogenic amino acids. In this aspect, the proteinogenic amino acid is alanine, cysteine, aspartic acid, glutamic acid, phenylalanine, glycine, histidine, isoleucine, lysine, leucine, methionine, asparagine, proline, glutamine, arginine, serine, threonine, valine, tryptophan, tyrosine, or a combination thereof. Further in this aspect, the non-proteinogenic amino acid is taurine, hydroxyproline, lanthionine, hydroxylysine, ornithine, or a combination thereof. In these aspects, consumption by a human or animal of a food or animal feed product containing a feedstock that has been microbially-fermented is beneficial to the consumer due to the additional nutrition provided by the increased crude protein, amino acids, or the combination thereof.

In one aspect, the nutraceutical composition has from 3% to 40%, 5% to 30%, or 5% to 20% by weight more protein compared to the same co-product not fermented with the species of *Monascus*. In another aspect, when corn whole stillage is fermented with *Monascus purpureus*, the nutraceutical composition has from 5% to 10% by weight more protein compared to the same co-product not fermented with *Monascus purpureus*.

In other aspects, production of one or more fatty acids can be enhanced using the methods described herein. In another aspect, the fatty acid may be myristic acid, myristoleic acid, pentadecanoic acid, palmitic acid, palmitoleic acid, margaric acid, cis-10-heptadecenoic acid, stearic acid, elaidic acid, oleic acid, vaccenic acid, linoleic acid, linolenic acid, stearidonic acid, arachidic acid, gonodic acid, homo-alpha-linolenic acid, arachidonic acid, 3n-arachidonic acid, eicosapentaenoic acid, behenoic acid, erucic acid, clupanodonic acid, docosahexaenoic acid, lignoceric acid, nervonic acid, or a combination thereof. In these aspects, consumption by a human or animal of a food or animal feed product containing the nutraceutical composition is beneficial to the consumer due to the additional nutrition provided by the increased fatty acids.

In one aspect, when corn whole stillage is fermented with purpureus, the nutraceutical composition has 10% to 20% by weight more palmitic acid compared to the same co-product not fermented with *Monascus purpureus*;

300% to 600% by weight more palmitoleic acid compared to the same co-product not fermented with *Monascus purpureus*;

150% to 250% by weight more stearic acid compared to the same co-product not fermented with *Monascus purpureus*;

20% to 40% by weight more oleic acid compared to the same co-product not fermented with *Monascus purpureus*;

400% to 500% by weight more DHA compared to the same co-product not fermented with *Monascus purpureus*;

350% to 550% by weight more lignoceric acid compared to the same co-product not fermented with *Monascus purpureus*.

In certain aspect, the methods described herein produce nutraceuticals not present in the co-product prior to fermentation with a species of *Monascus*. For example, when corn whole stillage is fermented with *Monascus purpureus*, myristoleic acid and stearidonic acid are produced and present in the nutraceutical composition, which are not present in corn whole stillage. Additionally, monacolin K and mevinolinic acid are produced, which are not present in the corn whole stillage prior to fermentation.

In a further aspect, both crude lipid or fat levels in the nutraceutical composition are reduced compared to the co-product prior to fermentation with a species of *Monascus*. For example, when corn whole stillage is fermented with *Monascus purpureus*, the nutraceutical composition has from 60% to 80% by weight less fat compared to the same co-product not fermented with *Monascus purpureus*.

Applications of Nutraceutical Compositions

Due to the fact that the nutraceutical compositions produced herein have either have enhanced amounts of nutraceuticals when compared to the co-product prior to fermentation and/or new nutraceuticals not present in the co-product, the nutraceutical compositions have applications in the health industry.

In one aspect, the nutraceutical compositions described herein can be used to manufacture animal feed with enhanced health benefits. The nutraceutical compositions produced herein can be added to any animal feed. The amount of nutraceutical composition and the selection of the animal feed can vary depending upon the application. In one aspect, the nutraceutical composition is added to the animal feed as a dry material. In this aspect, the dry nutraceutical composition can be mixed with the animal feed using techniques known in the art. Additional components or additives can be added to the nutraceutical composition and animal feed as needed. One advantage of the nutraceutical composition described herein is that the nutraceutical composition can be added directly the base animal feed without the need of performing additional extraction or separation steps. Other than drying the nutraceutical composition, the nutraceutical composition does not require any further processing in order to be incorporated into the animal feed. This provides numerous processing and economical advantages.

The animal feed with the nutraceutical compositions described herein can enhance or improve animal health compared to the same animal feed without the nutraceutical composition. For example, the animal feeds described can help reduce cholesterol levels in an animal due to the presence of monacalin K and mevinolinic acid present in the nutraceutical composition (and animal feed). Additionally, the presence of increased amounts of increased amounts of proteins, fatty acids, amino acids, and amino sugars added to the animal feed via the nutraceutical compositions described herein also impart additional health benefits.

In other aspects, the nutraceutical compositions described herein can be used in pharmaceutical applications. The methods described herein produce nutraceuticals not present in the co-product prior to fermentation. For example, monacolin K is produced when corn whole stillage is fermented with *Monascus purpureus*. In one aspect, described herein is a method for producing and isolating a nutraceutical of interest, where the method comprises (a) fermenting a species of *Monascus* in the presence of one or more co-products produced during corn ethanol fermentation, milo ethanol fermentation, or a combination thereof, and (b) isolating the nutraceutical of interest from the nutraceutical composition.

The nutraceutical of interest can be isolated from the nutraceutical composition using techniques known in the art. In one aspect, nutraceutical of interest can be extracted from the nutraceutical composition. The nutraceutical can be purified and/or concentrated by any means typically used for purifying and/or concentrating a single component from a complex mixture including, but not limited to: precipitation, column chromatography, flash chromatography, preparatory HPLC, affinity chromatography, ion exchange chromatography, electrophoresis, recrystallization, sublimation, distillation, extraction, filtration, centrifugation, vacuum evaporation, and combinations thereof. In a further aspect, multiple desired nutraceuticals can be extracted and purified from the same nutraceutical composition. Upon isolation of the nutraceutical, it can be formulated for human consumption using techniques known in the art.

In one aspect, when corn whole stillage is fermented with *Monascus purpureus*, monacolin K and mevinolinic acid are produced. In this aspect, monacolin K and mevinolinic acid can be isolated separately or collectively using techniques known in the art.

Throughout this application, various publications are referenced. The disclosures of these publications in their entireties are hereby incorporated by reference into this application in order to more fully describe the compounds, compositions, and methods described herein.

EXAMPLES

The following examples are put forth so as to provide those of ordinary skill in the art with a complete disclosure and description of how the compositions and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.), but some errors and deviations should be accounted for. Unless indicated otherwise, parts are parts by weight, temperature is in ° C. or is at ambient temperature, and pressure is at or near atmospheric. Numerous variations and combinations of reaction conditions, e.g., component concentrations, desired solvents, solvent mixtures, temperatures, pressures, and other reaction ranges and conditions can be used to optimize the product purity and yield obtained from the described process. Only reasonable and routine experimentation will be required to optimize such process conditions.

Example 1

Fermentation Conditions

In this Example, the fermentation of corn whole stillage by pigmented and non-pigmented *Monascus purpureus* is outlined. One pigmented *M. purpureus* strain (ATCC 16365) and one non-pigmented *M. purpureus* strain (ATCC 16357) were obtained from the American Type Culture Collection (ATCC; Manassas, Va.).

Figure 1:
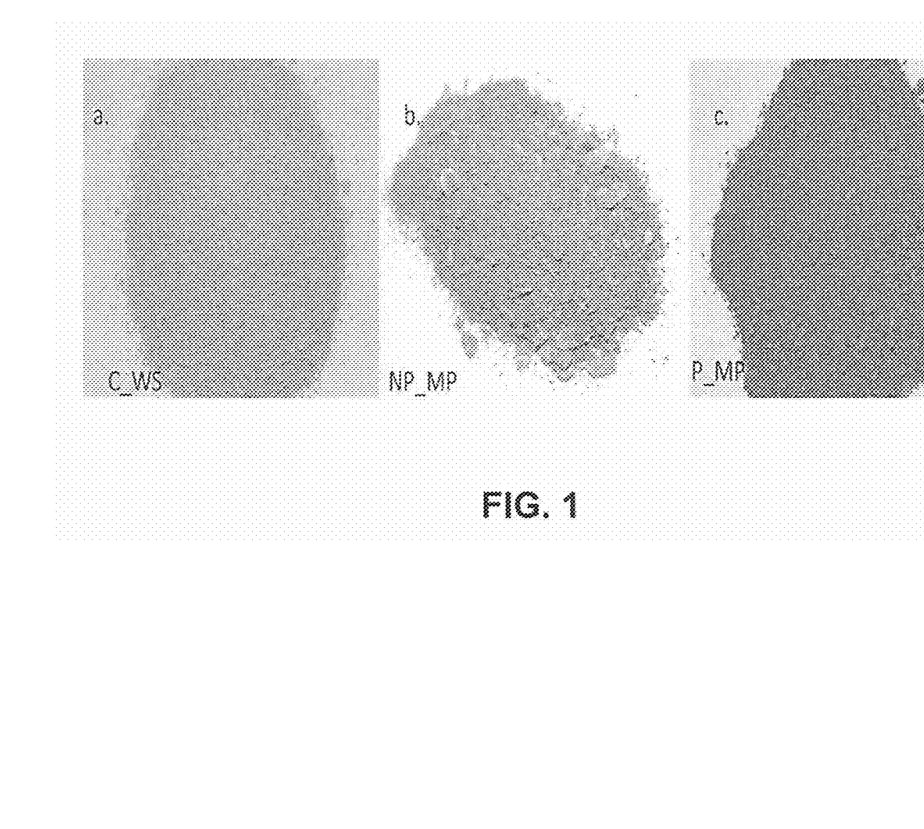
FIG. 1 shows freeze dried product produced by secondary fermentation of corn whole stillage by pigmented and non-pigmented *M. purpureus* species: (a) Control (no *M. purpureus*); (b) Non-pigmented *M. purpureus*; (c) Pigmented *M. purpureus*.

Submerged fermentation was carried out in shake flasks. One liter of medium contained 15% whole stillage (Center Ethanol Co., LLC, East St. Louis, Ill.), 1.5% corn steep liquor, 7.7% glycerol, and mineral salts (0.6 g $KH_2PO_4$, 0.3 g $MgSO_4$, 0.3 g $MnSO_4$, and 0.7 g $ZnSO_4$). The fermentation was carried out for 10 days with 200 rpm shaking at 30° C. Separate cultures were maintained for the pigmented and non-pigmented *M. purpureus* strains, and a negative control (i.e., whole stillage without any *Monascus* strains) was also maintained. Eight biological replicates per treatment were fermented; four replicates were pooled for further proximate analysis. Following fermentation, samples were freeze-dried and stored at −20° C. FIG. 1 shows representative freeze-dried samples for the control and both fungal cultures.

Example 2

Monacolin K (Lovastatin) Analysis by HPLC

Freeze-dried samples were extracted with acetonitrile, filtered using 0.4 μm filters, and 10 μL aliquots were injected via autosampler into a Shimadzu 2020 HPLC equipped with a dual wavelength UV detector. A 25 cm×4.6 mm C18 HPLC column was used for analysis. The mobile phase was isocratic (80:20 acetonitrile:water) with a flow rate of 1.5 mL/min A 238 nm wavelength was used for detection. A lovastatin standard (Sigma-Aldrich) was also used to determine retention time and concentration. A representative chromatogram can be seen in FIG. 2.

Figure 2:
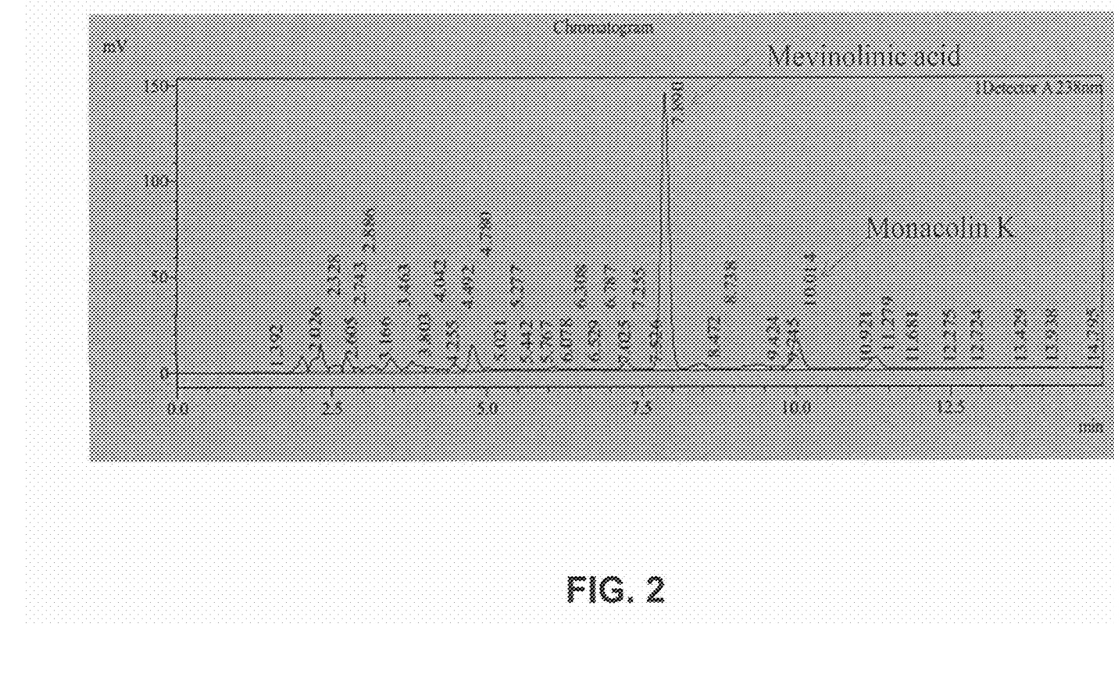
FIG. 2 is a chromatogram (UV-Vis absorption at 238 nm) showing peaks for monacolin K (lovastatin) and mevinolinic acid, a precursor compound for monacolin K, where the sample from secondary fermentation of whole corn stillage by pigmented *M. purpureus* was used to produce the chromatogram.

The pigmented and non-pigmented strains of *M. purpureus* both produced monacolin K (lovastatin) as well as the monacolin K precursor compound mevinolinic acid. Non-pigmented *M. purpureus* produced 1.71 mg/g monacolin K and pigmented *M. purpureus* produced 4.45 mg/g monacolin K.

Example 3

Proximate Analysis of Fermented Samples

Proximate analysis of fermented samples was conducted at the Agricultural Experiment Station Chemical Laboratory (AESCL) at the University of Missouri (Columbia, Mo.). Crude fat, fiber, protein, fatty acids, amino acids, glucosamine, glucose, and mannose were analyzed by routinely prescribed Association of Analytical Communities (AOAC) methods.

Table 1 shows proximate analyses of control (no *Monascus*) and *Monascus* fermented whole stillage for crude protein, acid detergent fiber, neutral detergent fiber, crude fat, glucosamine, glucose, and mannose. Means and standard errors are provided. Percent increase and/or percent decrease relative to controls are provided for both pigmented and non-pigmented *Monascus purpureus* cultures used for fermentation. Asterisks (*) indicate the maximum values determined for each category.

TABLE 1

Proximate Analysis of Control and *Monascus*-fermented Whole Stillage

| Proximate % | Control (no *Monascus*) | Non-Pigmented *M. purpureus* | Pigmented *M. purpureus* |
| --- | --- | --- | --- |
| Crude Protein | 24.77 ± 0.22 | 25.99 ± 0.28 (4.9% increase) | 27.30 ± 0.59* (10.2% increase) |
| Acid Detergent Fiber | 8.43 ± 0.18 | 17.43 ± 0.72 (106.8% increase) | 23.10 ± 0.58* (174% increase) |
| Neutral Detergent Fiber | 23.80 ± 0.04 | 31.22 ± 0.31 (31.2% increase) | 39.75 ± 1.11* (67% increase) |
| Crude Fat | 12.65 ± 0.02* | 4.65 ± 0.39 (63.2% decrease) | 3.06 ± 0.30 (76% decrease) |
| Glucosamine | 0.22 | 1.91 ± 0.10 (768% increase) | 2.47 ± 0.07* (1022% increase) |
| Glucose | 6.75 ± 0.63* | 3.42 ± 0.03 (49% decrease) | 4.38 ± 0.06 (35% decrease) |
| Mannose | 1.03 ± 0.13 | 2.89 ± 0.10 (180% increase) | 4.87 ± 0.28* (372% increase) |
| Monacolin K (mg/g) | 0.00 | 1.71 | 4.45* |

Both pigmented and non-pigmented *M. purpureus* cultures increased crude protein, fiber, glucosamine, and mannose content, compared to a control without secondary fermentation. Further, both pigmented and non-pigmented *M. purpureus* cultures reduced crude fat and glucose. In general, the pigmented fungus outperformed the non-pigmented strain.

Table 2 shows amino acid profiles of control (no *Monascus*) and *Monascus* fermented whole stillage. Asterisks (*) indicate the maximum values determined for each category.

TABLE 2

Amino Acid Profiles

| Amino Acid | Control (no *Monascus*) | Non-Pigmented *M. purpureus* | Pigmented *M. purpureus* |
| --- | --- | --- | --- |
| Taurine | 0.04 | 0.15* | 0.08 |
| Hydroxyproline | 0.14* | 0.03 | 0.03 |
| Aspartic Acid | 1.53 | 1.19 | 1.68* |
| Threonine | 0.91* | 0.71 | 0.86 |
| Serine | 0.94* | 0.62 | 0.77 |
| Glutamic Acid | 2.74* | 1.77 | 2.44 |
| Proline | 1.62* | 0.66 | 0.97 |
| Lanthionine | 0.00 | 0.00 | 0.00 |
| Glycine | 1.05* | 0.76 | 0.90 |
| Alanine | 1.62* | 1.15 | 1.26 |
| Cysteine | 0.46* | 0.29 | 0.41 |
| Valine | 1.35* | 0.87 | 1.31 |
| Methionine | 0.51* | 0.21 | 0.29 |
| Isoleucine | 0.96* | 0.54 | 0.79 |
| Leucine | 2.59* | 1.25 | 1.86 |
| Tyrosine | 0.83* | 0.60 | 0.80 |
| Phenylalanine | 1.22* | 0.63 | 0.86 |
| Hydroxylysine | 0.13* | 0.05 | 0.00 |
| Ornithine | 0.05* | 0.03 | 0.03 |

TABLE 2-continued

Amino Acid Profiles

| Amino Acid | Control (no Monascus) | Non-Pigmented M. purpureus | Pigmented M. purpureus |
|---|---|---|---|
| Lysine | 1.02* | 0.65 | 0.67 |
| Histidine | 0.68* | 0.28 | 0.38 |
| Arginine | 1.25* | 0.57 | 0.79 |
| Tryptophan | 0.25 | 0.22 | 0.29* |
| Total | 21.85* | 13.16 (40% decrease) | 17.43 (20% decrease) |

The total amino acid content was reduced in both the pigmented and non-pigmented samples compared to the control; a greater reduction in amino acids was seen with the non-pigmented sample.

Table 3 shows fatty acid profiles of control (no Monascus) and Monascus fermented whole stillage. Asterisks (*) indicate the maximum values determined for each category.

TABLE 3

Fatty Acid Profiles

| Fatty Acid | Control (no Monascus) | Non-Pigmented M. purpureus | Pigmented M. purpureus |
|---|---|---|---|
| Myristic (14:0) | 0.06* | 0.00 | 0.00 |
| Myristoleic (9c-14:1) | 0.00 | 1.49* | 0.63 |
| Pentadecanoic (15:0) | 0.00 | 0.00 | 0.00 |
| Palmitic (16:0) | 14.12 | 16.91* | 15.52 |
| Palmitoleic (9c-16:1) | 0.14 | 0.91* | 0.62 |
| Margaric (17:0) | 0.09 | 0.32* | 0.00 |
| 10c-heptadecenoic (10c-17:1) | 0.02* | 0.00 | 0.00 |
| Stearic (18:0) | 2.41 | 6.87 | 7.87* |
| Elaidic (9t-18:1) | 0.02* | 0.00 | 0.00 |
| Oleic (9c-18:1) | 25.77 | 31.43 | 34.31* |
| Vaccenic (11c-18:1) | 0.00 | 0.00 | 0.00 |
| Linoleic (18:2n6) | 54.21* | 31.30 | 32.98 |
| Linolenic (18:3n3) | 1.41* | 0.53 | 0.51 |
| Stearidonic (18:4n3) | 0.00 | 1.40* | 1.23 |
| Arachidic (20:0) | 0.44* | 0.23 | 0.00 |
| Gonodic (20:1n9) | 0.34* | 0.00 | 0.00 |
| Homo-alpha-linolenic (20:3n3) | 0.00 | 0.00 | 0.00 |
| Arachidonic (20:4n6) | 0.00 | 0.00 | 0.00 |
| 3n-arachidonic (20:4n3) | 0.00 | 0.00 | 0.00 |
| Eicosapentaenoic (20:5n3) | 0.00 | 0.00 | 0.00 |
| Behenoic (22:0) | 0.22 | 0.24* | 0.00 |
| Erucic (22:1n9) | 0.00 | 0.00 | 0.00 |
| Clupanodonic (22:5n3) | 0.00 | 0.00 | 0.00 |
| Docosahexaenoic (22:6n3) | 0.15 | 0.83* | 0.77 |
| Lignoceric (24:0) | 0.32 | 1.90* | 1.56 |
| Nervonic (24:1n9) | 0.00 | 0.00 | 0.00 |

Although crude fat was reduced by M. purpureus fermentation in both the pigmented and non-pigmented samples, production of some fatty acids (i.e., myristoleic acid, palmitic acid, palmitoleic acid, stearic acid, oleic acid, stearidonic acid, docosahexaeonic acid, and lignoceric acid) was enhanced in both M. purpureus samples, compared to the control.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A nutraceutical composition produced by the process comprising fermenting Monascus purpureus in the presence of one or more co-products produced during corn ethanol fermentation, milo ethanol fermentation, or a combination thereof.

2. The nutraceutical composition of claim 1, wherein the of Monascus purpureus is pigmented Monascus purpureus.

3. The nutraceutical composition of claim 1, wherein the Monascus purpureus is non-pigmented Monascus purpureus.

4. The nutraceutical composition of claim 1, wherein the co-product comprises corn whole stillage.

5. The nutraceutical composition of claim 1, wherein the co-product comprises dried distillers grains with solubles (DDGS).

6. The nutraceutical composition of claim 1, wherein after the fermentation step, the nutraceutical composition is not subsequently extracted.

7. The nutraceutical composition of claim 1, wherein the nutraceutical composition comprises monacolin K.

8. The nutraceutical composition of claim 1, wherein the nutraceutical composition comprises more protein compared to the same co-product not fermented with the Monascus purpureus.

9. The nutraceutical composition of claim 1, wherein the nutraceutical composition has less fat compared to the same co-product not fermented with the Monascus purpureus.

10. The nutraceutical composition of claim 1, wherein the nutraceutical composition comprises a higher amount of a fatty acid compared to the same co-product not fermented with the Monascus purpureus.

11. The nutraceutical composition of claim 10, wherein the said fatty acid is, palmitic acid, palmitoleic acid, stearic acid, oleic acid, docosahexaenoic and lignoceric acid.

12. The nutraceutical composition of claim 1, wherein the nutraceutical composition comprises myristoleic acid and stearidonic acid.

13. The nutraceutical composition of claim 1, wherein the fermentation step is conducted in a fed batch process, a continuous process, a semi-solid process, a solid-state process, or a submerged process.

14. An animal feed comprising the nutraceutical composition of claim 1.

15. The animal feed of claim 14, wherein the feed is poultry feed, ruminant feed, non-ruminant feed, horse feed, cattle feed, aquaculture feed, or pet food.

16. A process for producing a nutraceutical composition, the process comprising fermenting a Monascus purpureus in the presence of one or more by-products produced during corn ethanol fermentation, milo ethanol fermentation, or a combination thereof.

* * * * *